(12) United States Patent
Lin et al.

(10) Patent No.: US 10,980,620 B2
(45) Date of Patent: Apr. 20, 2021

(54) REINFORCED RESIN-RETAINED BRIDGE

(71) Applicant: JTI Biomed Corp., Tainan (TW)

(72) Inventors: Luh-Yuan Lin, Winnetka, IL (US); Jiin-Huey Chern Lin, Winnetka, IL (US); Chien-Ping Ju, Kansas City, MO (US); Yen-Chun Chen, Kaohsiung (TW)

(73) Assignee: JOY MEDICAL DEVICES CORPORATION, Kaohsiung (TW)

( * ) Notice: Subject to any disclaimer, the term of this patent is extended or adjusted under 35 U.S.C. 154(b) by 281 days.

(21) Appl. No.: 15/959,373

(22) Filed: Apr. 23, 2018

(65) Prior Publication Data

US 2018/0311020 A1    Nov. 1, 2018

Related U.S. Application Data

(60) Provisional application No. 62/490,171, filed on Apr. 26, 2017.

(51) Int. Cl.
| | | |
|---|---|---|
| *A61C 13/271* | (2006.01) | |
| *A61L 27/36* | (2006.01) | |
| *A61C 13/275* | (2006.01) | |
| *A61C 7/20* | (2006.01) | |
| *A61C 13/00* | (2006.01) | |
| *A61C 13/087* | (2006.01) | |

(52) U.S. Cl.
CPC ............ *A61C 13/26* (2013.01); *A61C 13/275* (2013.01); *A61L 27/3641* (2013.01); *A61C 7/20* (2013.01); *A61C 13/0003* (2013.01); *A61C 13/087* (2013.01)

(58) Field of Classification Search
CPC ..... A61C 13/26; A61C 13/275; A61C 13/087; A61C 13/0003; A61C 7/20; A61L 27/3641
USPC ....................................... 433/201.1
See application file for complete search history.

(56) References Cited

U.S. PATENT DOCUMENTS

| | | | | | |
|---|---|---|---|---|---|
| 4,360,342 | A | * | 11/1982 | Salvo ..................... | A61C 13/26 433/172 |
| 4,380,435 | A | * | 4/1983 | Raeder ................... | A61C 13/26 433/180 |
| 4,504,229 | A | * | 3/1985 | Garito .................... | A61C 5/007 433/215 |
| 4,531,566 | A | * | 7/1985 | Boettcher .......... | A61C 13/0003 164/246 |

(Continued)

FOREIGN PATENT DOCUMENTS

| | | | |
|---|---|---|---|
| JP | 2005192722 | * | 7/2005 |
| JP | 2005192722 | A | 7/2005 |
| WO | 94 08783 | A1 | 4/1994 |

*Primary Examiner* — Matthew M Nelson
(74) *Attorney, Agent, or Firm* — Bacon & Thomas, PLLC

(57) ABSTRACT

A resin-retained denture bridge having an improved bonding between a false tooth or teeth of the bridge and a retainer wire of the bridge is provided in the present invention, wherein a coupling recess is formed on a lingual side of the false tooth and a protrusion or an omega-shaped bend is formed on the retainer wire. The protrusion or omega-shaped bend is received in the coupling recess of the false tooth after or prior to a resin being filled in the coupling recess, which is then cured to form a secure engagement, so that the false tooth is bonded to the retainer with the end portions of the retainer wire extending laterally from the false tooth.

11 Claims, 6 Drawing Sheets

(56) References Cited

U.S. PATENT DOCUMENTS

| | | | | |
|---|---|---|---|---|
| 4,820,157 | A * | 4/1989 | Salvo | A61K 6/884 |
| | | | | 433/180 |
| 5,000,687 | A * | 3/1991 | Yarovesky | A61C 13/0003 |
| | | | | 433/180 |
| 5,194,001 | A * | 3/1993 | Salvo | A61C 5/30 |
| | | | | 433/180 |
| 5,772,438 | A * | 6/1998 | Deom | A61C 13/26 |
| | | | | 433/181 |
| 5,888,068 | A * | 3/1999 | Lans | A61C 13/26 |
| | | | | 433/181 |
| 5,921,778 | A * | 7/1999 | Karmaker | A61C 5/007 |
| | | | | 433/215 |
| 6,200,136 | B1 * | 3/2001 | Prasad | A61C 13/26 |
| | | | | 433/180 |
| 6,916,178 | B2 * | 7/2005 | Lans | A61C 5/007 |
| | | | | 433/181 |
| 2011/0091838 | A1 * | 4/2011 | Yoon | A61C 13/275 |
| | | | | 433/171 |
| 2012/0178046 | A1 * | 7/2012 | Lans | A61C 13/275 |
| | | | | 433/172 |

* cited by examiner

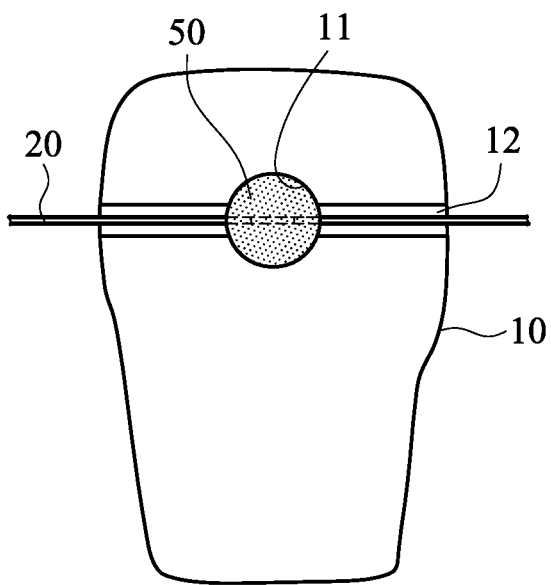
Fig. 4a
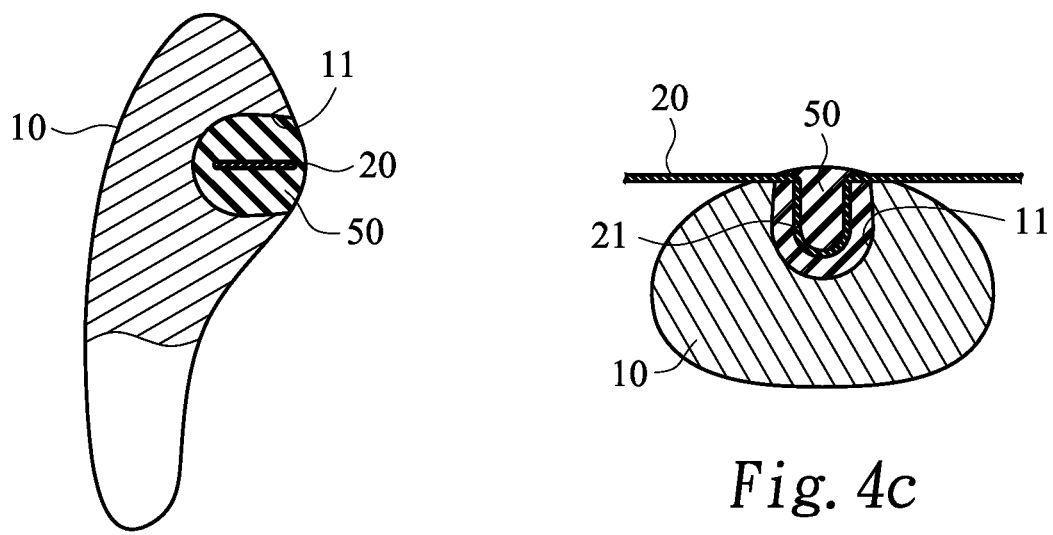
Fig. 4b
Fig. 4c

US 10,980,620 B2

REINFORCED RESIN-RETAINED BRIDGE

CROSS-REFERENCE TO RELATED APPLICATIONS

This patent application is a non-provisional of U.S. provisional patent applications Ser. No. 62/490,171 filed on Apr. 26, 2017, which is incorporated herein by reference.

FIELD OF THE INVENTION

The present invention is related to a reinforced resin-retained bridge for installing a false tooth or teeth in a patient's mouth having a missing tooth or teeth between two healthy teeth.

BACKGROUND OF THE INVENTION

Maryland bridge is a popular resin-retained bridge (a fixed dental prosthesis) replacing a missing tooth that relies for its retention on a composite resin cement. This special bridge is designed for temporary use, for example, between the implantation of a dental implant root and the installation of the abutment (for the two-stage design), normally 4-6 months or longer, depending on osteointegration process of the patient. However, the false tooth retained by the bridge falls accidently, for example an occlusion on hard food during the patient's chewing, or even falls due to a gradually weakening bonding between the false tooth and the retainer.

SUMMARY OF THE INVENTION

A primary objective of the present invention is to provide a reinforced resin-retained bridge having an improved bonding between a false tooth or teeth of the bridge and a retainer of the bridge.

Another objective of the present invention is to provide a method of installing a false tooth or teeth in a patient's mouth having a missing tooth or teeth between two healthy teeth.

Preferred embodiments of the present invention include (but not limited to) those set forth in the following claims.

BRIEF DESCRIPTION OF THE DRAWINGS

FIG. 1b is a schematic partial cross-sectional view of the false tooth shown in FIG. 1a.

FIG. 4a is a schematic lingual side view of a false tooth coupled with a retainer wire prepared in accordance with the first preferred embodiment of the present invention.

FIG. 4b is a schematic vertical partial cross-sectional view of the false tooth coupled with the retainer wire shown in FIG. 4a.

FIG. 4c is a schematic horizontal cross-sectional view of the false tooth coupled with the retainer wire shown in FIG. 4a.

DETAILED DESCRIPTION OF THE INVENTION

A reinforced resin-retained bridge having an improved bonding between a false tooth or teeth of the bridge and a retainer wire of the bridge is disclosed in the present invention, which is brought about by providing a coupling recess on a lingual side of the false tooth and forming a protrusion or an omega-shaped bend on the retainer wire. The protrusion or omega-shaped bend is received in the coupling recess of the false tooth after or prior to a resin being filled in the coupling recess, which is then cured to form a secure engagement, so that the false tooth is bonded to the retainer with the end portions of the retainer wire extending laterally from the false tooth.

EXAMPLE 1

Direct Composite Resin Bridge Clinical Procedures

1. Acrylic tooth selection and preparation

Figure 1A:
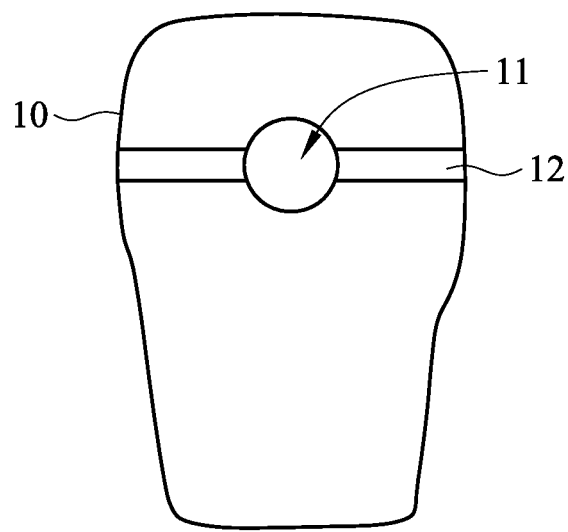
FIG. 1a is a schematic lingual side view of a false tooth prepared in accordance with a first preferred embodiment of the present invention.
Figure 1B:
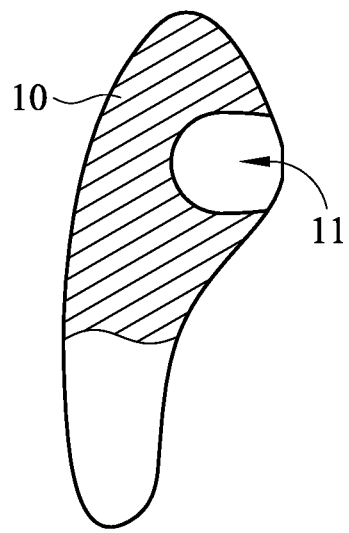
Figure 2:
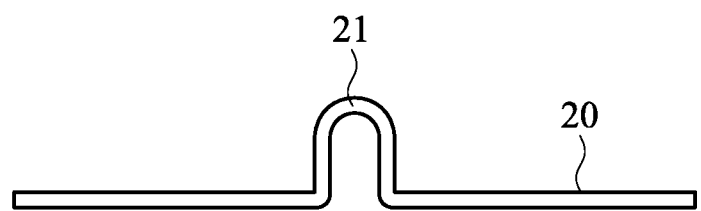
FIG. 2 is a schematic perspective view of a retainer wire prepared in accordance with the first preferred embodiment of the present invention.

Firstly, the replacement acrylic tooth 10 was chosen according to the shape and mould of the missing tooth. After the acrylic tooth 10 was selected, a round shaped hole 11 of 2 to 3 mm diameter and about 2 mm deep was prepared at the lingual side of the tooth in between ½ to ⅓ gingivally. A horizontal groove 12 about 1 to 2 mm wide and 2 to 3 mm deep from a mesial border to a distal border of the tooth and across the hole 11 was prepared, as shown in FIG. 1a and FIG. 1b.

2. Retainer wire preparation

A size 0.030" (0.76 mm) retainer wire 20 was chosen, and a small omega-shaped (1 to 2 mm) bend 21 was prepared at about the middle of the wire 20, so that the retainer wire 20 will fit the hole 11 and the groove 12 of the acrylic tooth 10, as shown in FIG. 2 and FIG. 4a to FIG. 4c.

3. Secure the retainer wire

The retainer wire 20 was attached to the lingual side of the acrylic tooth 10 with the omega-shaped bend 21 being engaged with the hole 11, and the wire 20 being aligned with the groove 12 of the acrylic tooth. The engagement was secured by applying the tooth shade self-curing acrylic resin 50 inside the hole 11 only, not in the groove.

4. Retention grooves on the abutment teeth

Figure 3:
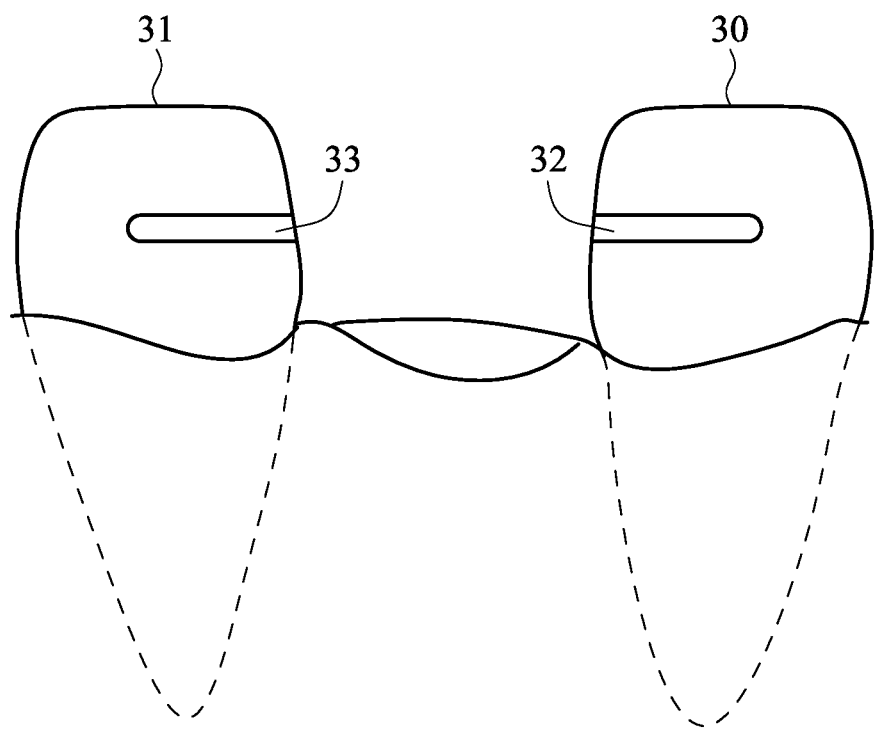
FIG. 3 is a schematic lingual side view of abutment teeth with retention grooves prepared in accordance with the first preferred embodiment of the present invention.

The acrylic tooth 10 with the retainer wire 20 was tried in the mouth to determine the position of retention grooves 32, 33 on the abutment teeth 30, 31. The retainer wire extension was adjusted to a right length. As shown in FIG. 3, the retention grooves 32, 33 were prepared on the abutment teeth 30, 31 corresponding to the retainer wire extension, so that portions of the retainer wire 20 extending laterally from the acrylic tooth 10 are able to be accommodated in the retention grooves 32, 33.

5. Installing

Figure 5:
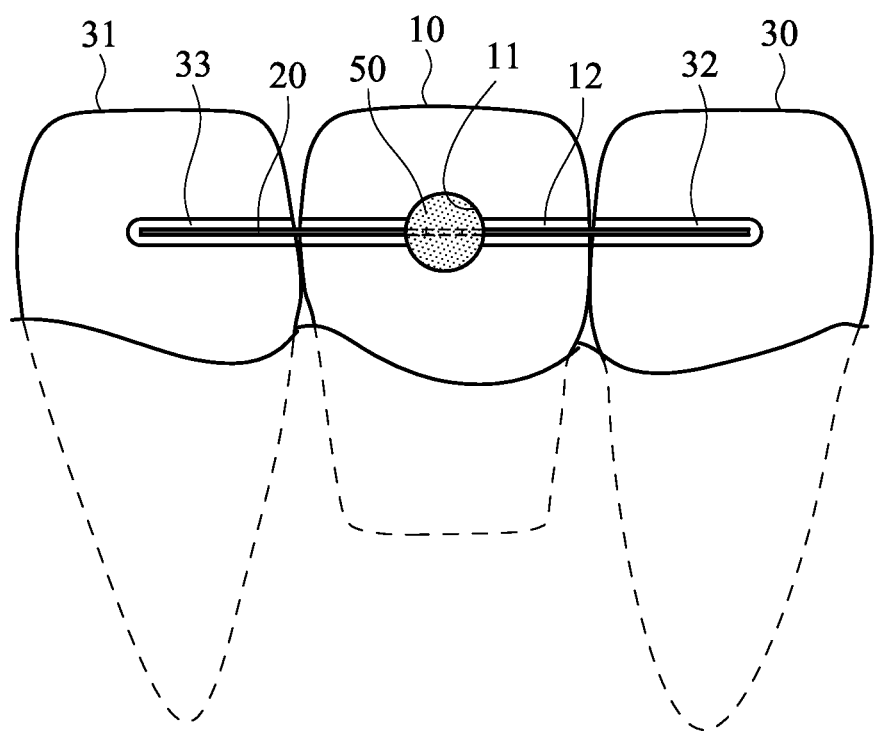
FIG. 5 is a schematic lingual side view of a reinforced resin-retained bridge installed between two abutment teeth in accordance with the first preferred embodiment of the present invention.

The abutment teeth 30, 31 were scaled if necessary, and cleaned with pumice and water in a rubber cup. The enamel in the retention grooves 32, 33 of the abutment teeth was etched with 37% phosphoric acid, washed, dried and coated with an enamel bonding solution using a small brush. The acrylic tooth 10 with its retainer wire 20 was installed between the abutment teeth 30, 31 with the portions of the retainer wire 20 extending laterally from the acrylic tooth (wings) being accommodated in the retention grooves 32, 33 of the abutment teeth 30, 31, as shown in FIG. 5. The acrylic tooth 10 with its retainer wire 20 were secured to the abutment teeth 30, 31 by applying a composite resin (not shown in the drawings) followed by light curing for 20-40 seconds. Occlusion was checked and make sure that there was no interference in centric occlusion or excursive movements of the mandible.

6. Final Polishing

Final polishing of the prosthesis was carried out using graded burs, strips and discs.

In step 3 of the above procedures, the sequence of engaging the retainer wire to the acrylic tooth and applying the tooth shade self-curing acrylic resin may be altered. In this alternative, the tooth shade self-curing acrylic resin was injected into the hole first, and then the retainer wire was attached to the lingual side of the acrylic tooth with the omega-shaped bend being engaged with the hole filled with the acrylic resin.

Another alternative is the retainer wire instead of consisting of a single core is a stranded wire, or even a mesh band with a greater flexibility. The omega-shaped bend formed with a single core retainer wire may be avoided, when the stranded wire, or the mesh band is used as the retainer wire, because the stranded wire or the mesh band are able to be pushed into the hole of the acrylic tooth with a burnisher right after the retainer wire is attached to the lingual side of the acrylic tooth.

It is apparent that the time for completing the Clinical Procedures described above can be saved dramatically, if a set of pre-manufactured acrylic teeth of different sizes and shades are readily available for selection, wherein the pre-manufactured acrylic tooth contains the embedded retainer wire with wings, as prepared in accordance with steps 2 and 3 of the Clinical Procedures or the aforesaid alternatives.

EXAMPLE 2

Clinical Procedures

1) Acrylic Tooth Selection and preparation

Firstly, the acrylic tooth was chosen according to the shade and mold of the missing tooth's adjacent teeth. After the acrylic tooth was decided, a round-shaped hole of 2 to 3 mm in diameter and about 2 mm in depth was prepared to the cingulum areas of the lingual surface. A horizontal groove was formed from the hole to the mesial and distal surface of the acrylic resin tooth at a depth of about 3 mm in width and 2 mm in depth as shown in FIGS. 1a and 1b.

2) Retainer Mesh preparation.

Figure 6:
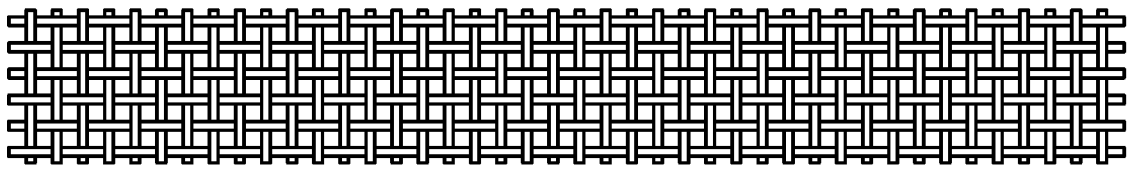
FIG. 6 is a schematic drawing showing a stainless-steel wire mesh used in a preferred embodiment of the present invention.

A stainless-steel wire mesh of 0.5 mm thickness and 3 mm width as shown in FIG. 6 was used, which is sold with a trademark of Masel®. A length of 20 mm of the mesh was prepared, and placed in the horizontal groove of the acrylic tooth with its center being adapted to the central hole by 1 mm burnisher. Then it was secured by applying the tooth shade self-curing acrylic resin at the hole area only, not in the groove area.

3) Acrylic tooth with its retainer mesh wings was tried in the mouth to check any occlusion interference and the retainer wings shall cover ⅔ of the tooth width of the abutment tooth. The retainer mesh shall be trimmed to its suitable size. If there was an interference, a groove will be placed at the abutment natural teeth. If this procedure was needed, the local anesthesia will be administrated and horizontal grooves were prepared into the lingual surfaces of the abutment teeth.

4) Bonding

The abutment teeth were scaled if necessary, and cleaned with pumice and water in a rubber cup. The enamel of the abutment teeth was etched with 37% phosphoric acid for 5 seconds, washed, dried and then coated with an enamel bonding solution using a small brush. The acrylic tooth with its retainer mesh wings was installed between the abutment teeth and was secured by applying the composite resin followed by light curing for 20 to 40 seconds. Occlusion was checked and made sure that there was no interference in centric occlusion or excursive movements of the mandible.

5) Final Polishing

Final polishing of the prosthesis was carried out using graded burs, strips and discs.

The invention claimed is:

1. A reinforced resin-retained bridge comprising a single false tooth formed as a single unitary body, and a retainer, wherein the false tooth is provided with a coupling recess on a lingual side thereof, and the retainer has two end portions and is provided with one engaging means between the two end portions corresponding to the coupling recess, wherein the one engaging means is fixedly connected to the coupling recess of the false tooth, so that said false tooth is bonded to the retainer with the end portions of the retainer extending laterally from said false tooth,
wherein the retainer comprises a metal mesh band, a stranded wire or a single core metal wire, and the engaging means comprises a deformed portion of the metal mesh band or the stranded wire adapted to be pressed into the coupling recess, or a protrusion or an omega-shaped bend formed on the single core metal wire having a shape and a size adapted to be fit in the coupling recess.

2. The reinforced resin-retained bridge of claim 1, wherein the coupling recess is a cavity.

3. The reinforced resin-retained bridge of claim 2, wherein the cavity has an opening on the lingual side and an enlarged inner space following the opening.

4. The reinforced resin-retained bridge of claim 2, wherein the retainer is the metal mesh band or the stranded wire, and the engaging means comprises the deformed portion of the metal mesh band or the stranded wire and a resin filled in the coupling recess and covering the metal mesh band or the stranded wire which are pressed into the coupling recess.

5. The reinforced resin-retained bridge of claim 3, wherein the retainer comprises the single core metal wire, and the engaging means comprises the protrusion or the omega-shaped bend formed on the single core metal wire, and a resin filled in the coupling recess and said resin adheres the protrusion or the omega-shaped bend of the single core metal wire to the false tooth.

6. The reinforced resin-retained bridge of claim 4, wherein the false tooth is further provided with a groove extending from a mesial border to a distal border and across the coupling recess of the false tooth, and the metal mesh band or stranded wire are accommodated in the groove while the deformed portion of the metal mesh band or the stranded wire is pressed into the coupling recess.

7. The reinforced resin-retained bridge of claim 5, wherein the false tooth is further provided with a groove extending from a mesial border to a distal border and across the coupling recess of the false tooth, and the single core metal wire is accommodated in the groove while the protrusion or the omega-shaped bend of the single core metal wire is fit in the coupling recess.

8. The reinforced resin-retained bridge of claim 6 further comprising a composite resin covering the metal mesh band or stranded wire accommodated in the groove.

9. The reinforced resin-retained bridge of claim 7 further comprising a composite resin covering the single core metal wire accommodated in the groove.

10. A method of installing a single false tooth formed as a single unitary body in a patient's mouth having a missing tooth between two healthy teeth comprising:
   preparing a reinforced resin-retained bridge as set forth in claim 1;
   applying an enamel bonding solution to a lingual side of each of the two healthy teeth for bonding the end portions of the retainer;
   inserting the reinforced resin-retained bridge between the two healthy teeth with the end portions of the retainer contacting the enamel bonding solution applied to the lingual sides of the two healthy teeth;
   applying a composite resin to cover the end portions of retainer and at least a portion of the lingual sides of the two healthy teeth, so that no portion of the retainer is exposed in the patient's mouth; and
   curing the composite resin.

11. The method of claim 10 further comprising:
   forming a groove on the lingual side of each of the two healthy teeth before said enamel bonding solution being applied;
   wherein said enamel bonding solution is applied to the grooves formed on the lingual sides of the two healthy teeth.

\* \* \* \* \*